United States Patent [19]

Matsushima

[11] Patent Number: 4,561,604

[45] Date of Patent: Dec. 31, 1985

[54] SPINNING REEL

[75] Inventor: Shiro Matsushima, Sakai, Japan

[73] Assignee: Shimano Industrial Company Limited, Osaka, Japan

[21] Appl. No.: 631,758

[22] Filed: Jul. 17, 1984

[30] Foreign Application Priority Data

Jul. 18, 1983 [JP] Japan ................................ 58-111290

Dec. 26, 1983 [JP] Japan ................................ 58-203171

[51] Int. Cl.[4] .............................................. A01K 89/01

[52] U.S. Cl. ........................ 242/84.2 R; 242/84.21 R; 242/84.1 K

[58] Field of Search ..................... 242/84.1 K, 84.1 R, 242/84.2 R, 84.2 G, 84.2 F, 84.21 R, 84.21 A

[56] References Cited

U.S. PATENT DOCUMENTS 2,884,211 4/1959 Holahan, Jr. .................. 242/84.1 K 3,254,861 6/1966 Jahn ............................ 242/84.21 R 4,061,288 12/1977 Karlsson et al. ............... 242/84.2 R 4,106,718 8/1978 Catignani ...................... 242/84.2 R 4,418,877 12/1983 Nakajima ..................... 242/84.21 R

*Primary Examiner*—Billy S. Taylor

*Attorney, Agent, or Firm*—Stevens, Davis, Miller & Mosher

[57] ABSTRACT

A spinning reel includes a rotary frame which has a pair of support arms and which is supported rotatably to a reel body so that the rotary frame can rotate to wind up a fishing line onto a spool which is reciprocable longitudinally relative to the reel body. The reel includes an intercepting mechanism having an intercepter for intercepting the fishing line to prevent the line from entering through gaps located between the inner flange of the spool and the support arms to such an extent that the line reaches the root sides at which the support arms are connected to the main portion of the rotary frame. The intercepter also has engaging portions engageable with the support arms so that the intercepter rotates with respect to the spool by following the rotation of the rotary frame thereby preventing the line from entering through the gaps into the root sides of the support arms.

7 Claims, 7 Drawing Figures

FIG. 4
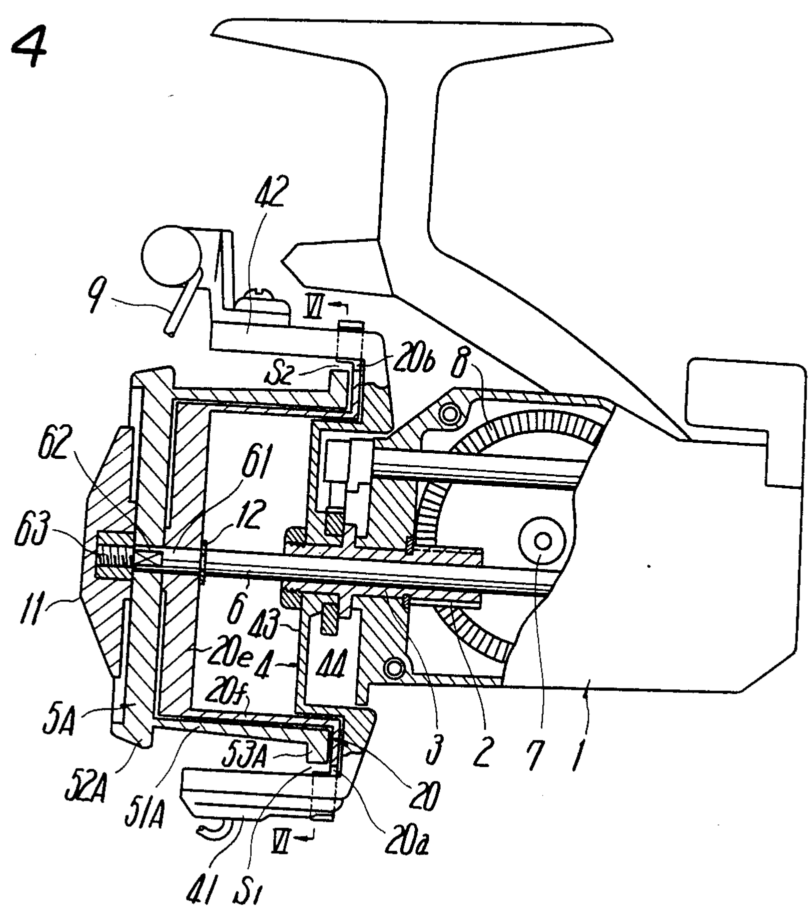
FIG. 5
FIG. 6
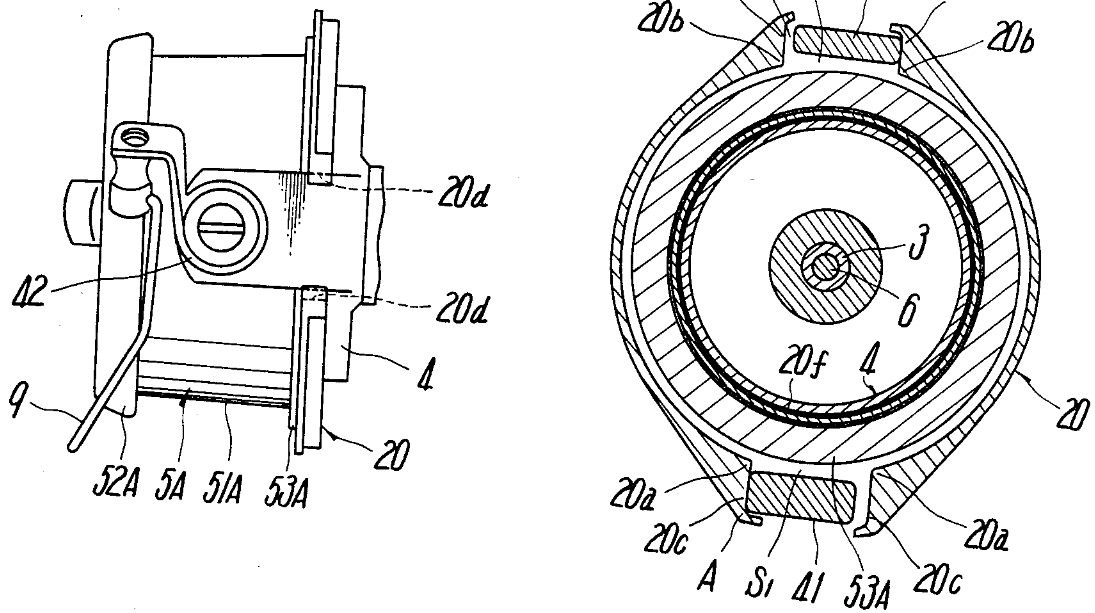

SPINNING REEL

FIELD OF THE INVENTION

This invention relates to a spinning reel, and more particularly to a spinning reel provided with a reel body, a rotary frame having a pair of support arms supported rotatably to the reel body, and a spool, so that the rotary frame rotates to wind up a fishing line onto the spool.

BACKGROUND OF THE INVENTION

Spinning reels generally include a spool which has a trunk and outer and inner flanges extending radially outwardly from both axial ends of the spool. The spool is supported to the reel body in relation of being movable longitudinally thereof. A rotary frame is provided between the spool and the reel body and has a pair of support arms opposite to each other at a phase difference of 180°, with the support arms extending toward the spool and opposite to the outer periphery of the spool's inner flange at the reel body side so that the fishing line is guided by a bail arm mounted across the utmost ends of the support arms and is wound onto the spool.

Such spinning reels have, between the inner flange of the spool and the support arms, gaps for preventing the line from contacting with the support arms even when the line is wound into a lump larger in an outer diameter than the inner flange of the spool.

The bail arm is turned to put the line in a released position and the line is drawn out from the spool for casting. Hence, upon finishing the casting, the line becomes loose so as to enter the aforesaid gaps and fall into the inside of the root portions of each support arm, resulting in that the line may often become entangled with the rotary frame or the spool shaft.

Hence, a spinning reel as disclosed in the Japanese Utility Model Publication No. 55,562 of 1980 has been proposed, which is provided at the outer periphery of the inner flange at the spool with an annular projection extending radially outwardly of the spool to thereby diminish the aforesaid gaps and prevent the line from falling into the inside of the inner flange at the spool through the gaps.

Such conventional spinning reel, however, is limited merely to a diminution in the gap between the inner flange at the spool and each support arm, thereby involving a problem in that it is not sure to prevent the line from entering the gaps.

SUMMARY OF THE INVENTION

An object of the invention is to provide a spinning reel where there is no danger that the fishing line will enter inside the spool through the gaps between the inner flange at the spool and the support arms, even when the gaps are very large.

The invention includes an intercepter rotatable together with the rotary frame, which is used to completely close the gaps between the inner flange and the support arms at the rotary frame regardless of error in the working accuracy of both the members, thereby ensuring the prevention of the line's entering inside the spool through the gaps.

This invention is characterized in that the spinning reel, which is provided with a reel body, a rotary frame supported rotatably thereto and having a pair of support arms, and a spool having a trunk and outer and inner flanges and supported to the reel body in relation of being movable longitudinally thereof to thereby wind up the line through the rotation of rotary frame, is provided with an intercepting mechanism having an intercepter to intercept the line to prevent the line from entering into the root side of each support arm through a gap between the inner flange at the spool and each support arm. The intercepter is supported rotatably with respect to the spool and is provided with an engaging portion engageable with at least one side surface of at least one support arm to thereby allow the intercepter to rotate together with the rotary frame.

The intercepter in the present invention is mounted to the outer periphery of the inner flange at the spool or the spool shaft therefor and engages with the support arms at the rotary frame to be rotatable together therewith, whereby the gaps between the inner flange and the support arms are surely closed to prevent an entrance of the line inside the spool. The intercepter of the invention, is an embodiment wherein it is supported rotatably to the spool, is fitted into an annular groove provided at the inner flange of the spool, and preferably, at the outer periphery of a cylindrical portion at the inner flange of the spool. The intercepter moves longitudinally of the reel body in association with the spool. On the other hand, the intercepter, in the embodiment wherein it is supported rotatably to the spool shaft, has its axial movement with respect thereto stopped by a stop means provided at the spool shaft. Thus, the intercepter moves longitudinally of the reel body in association with the spool when the line is wound onto the spool. As a result the intercepter, even when the spool is positioned at any longitudinal position relative to the reel body, can prevent the line from entering at the gaps into the area between the inner flange of the spool and the root ends of the support arm of the rotary frame.

Other objects and aspects of the invention will become apparent from the following description of various embodiments thereof with reference to the accompanying drawings in which:

BRIEF DESCRIPTION OF THE DRAWINGS

FIG. 4 is a partially cutaway side view of a second embodiment of the spinning reel of the invention, FIG. 5 is a partially omitted plan view of the FIG. 4 embodiment, FIG. 6 is a partially omitted sectional view taken on the line VI—VI in FIG. 4.

DETAILED DESCRIPTION OF THE INVENTION

Figure 1:
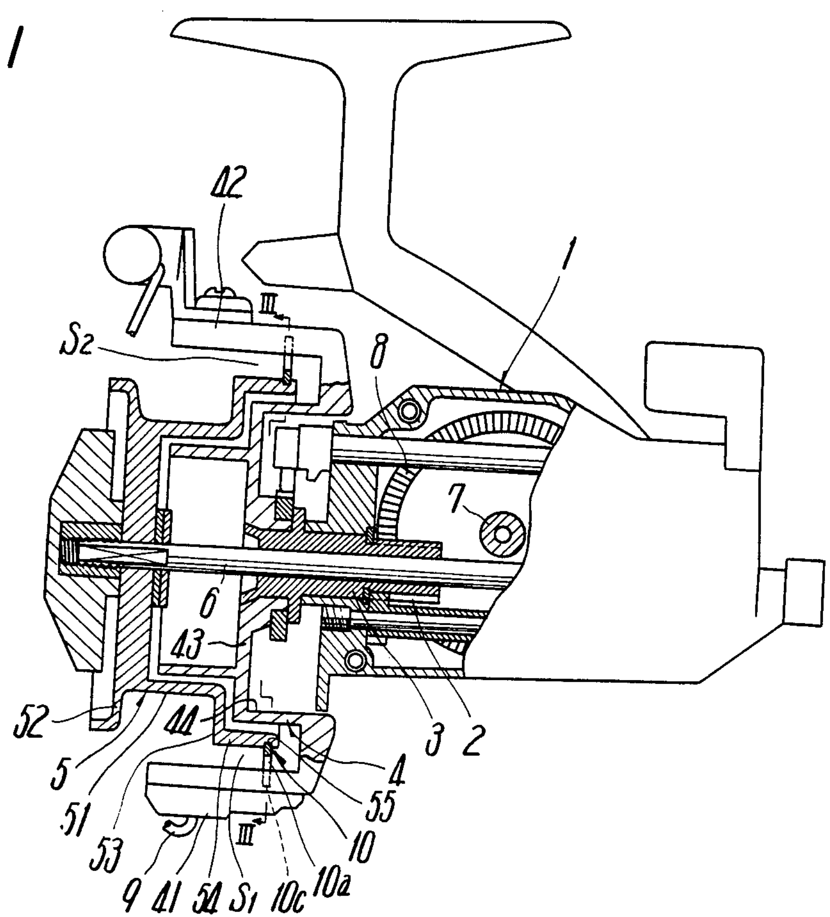
FIG. 1 is a partially cutaway side view of a first embodiment of a spinning reel of the invention.
Figure 2:
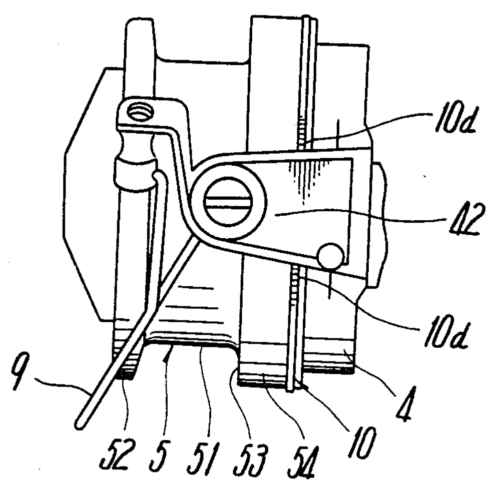
FIG. 2 is a partially omitted plan view of the FIG. 1 embodiment.
Figure 3:
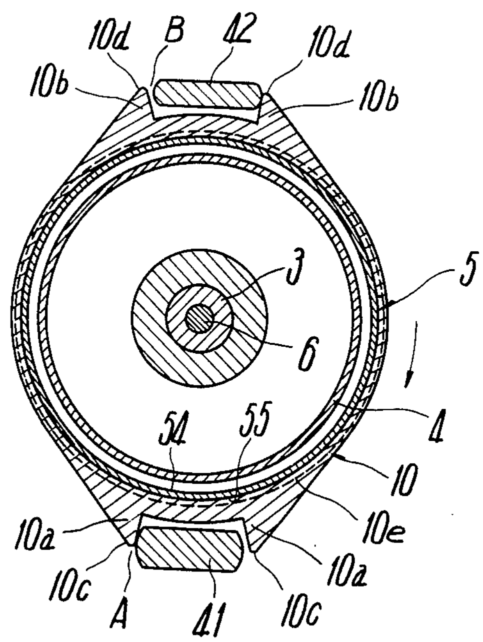
FIG. 3 is a sectional view taken on the line III—III in FIG. 1.

Referring to FIGS. 1 through 3, a typical embodiment of a spinning reel of the invention is shown, which is identical in basic construction with the well-known spinning reel. The spinning reel is basically constructed such that a hollow reel body 1 has at the upper surface a mounting leg for a fishing rod and at the front side a through bore. A tubular drive shaft 3 carrying a pinion 2 through a bearing is supported rotatably into the through bore, and a rotary frame 4 having a pair of support arms 41 and 42 is mounted onto the outer periphery of an utmost end of drive shaft 3. A spool shaft 6 having a spool 5 is supported into a central bore at the drive shaft 3 in relation of being movable longitudinally of reel body 1, and a handle shaft 7 extending perpendicularly to the axis of drive shaft 3 is supported rotatably to a side wall of reel body 1. A master gear 8 in mesh with the pinion 2 is mounted to the projecting end of handle shaft 7 within the reel body 1, and a handle (not shown) is provided at the outwardly projecting end of the handle shaft 7, so that the handle is rotated to drive the drive shaft 3 and rotate the rotary frame 4. Spool 5 moves longitudinally of the reel body 1 through a reciprocation mechanism (not shown), thereby guiding the line onto the spool 5 through a bail arm 9 mounted across the ends of support arms 41 and 42 and winding it onto the spool 5. The spool 5 comprises a trunk 51 on which the line is wound and outer and inner flanges 52 and 53 extending radially outwardly from both axial ends of trunk 51, with the inner flange 53 providing a cylindrical portion 54 sleeved onto the outer periphery of the front end of rotary frame 4. The rotary frame 4 comprises a disc-like portion 43 having a shaft bore for the drive shaft 3, a cylindrical portion 44 extending from the outer periphery of disc-like portion 43 toward the reel body 1, and the support arms 41 and 42 extending axially outwardly from the end of cylindrical portion 44. Rotary frame 4 is disposed between the spool 5 and the reel body 1, the support arms 41 and 42 being opposite to the outer periphery of cylindrical portion 54 at the inner flange 53 of the spool 5.

The spinning reel of the invention constructed as described above is provided with an intercepting mechanism including the intercepter 10 having intercepting portions 10*a* and 10*b* to intercept the line to prevent it from entering at the gaps $S_1$ and $S_2$ between the inner flange 53 and the support arms 41 and 42 into the root sides thereof with respect to the disc-like portion 43. The intercepter 10 in the first embodiment is supported rotatably onto the outer peripheral surface of cylindrical portion 54 at the inner flange 53 of spool 5 and is provided with engaging portions 10*c* and 10*d* engageable with one side surface of each support arm 41 or 42 in the rotation direction thereof and allowing the intercepter 10 to rotate together with the rotary frame 4.

In further detail, an annular groove 55 is provided on the outer periphery of cylindrical portion 54 at the inner flange 53, into which groove 55 the intercepter 10 is rotatably supported relative to spool 5. The intercepter 10 is ring-like-shaped, and has at the inner periphery a fitting portion 10*e* mainly annular and engageable with the annular groove 55. Intercepter 10 has at the outer periphery the intercepting positions 10*a* and 10*b*, with engaging portions 10*c* and 10*d* at the utmost ends of intercepting portions 10*a* and 10*b* respectively, so that one engaging portion 10*c* and the other engaging portion 10*d* engage with either one side surface of each support arm 41 or 42 in the normal or reverse rotation direction thereof, thereby rotating the intercepter 10 together with the rotary frame 4. The engaging portions 10*c* and 10*d* engage with the support arms 41 and 42 to avoid a shift of intercepting portion 10*a* or 10*b* in the rotation direction with respect to the arms 41 and 42, and the fitting portion 10*e* fitted into the annular groove 55 allows the intercepter 10 to associate with the spool 5 in longitudinal movement and move along the support arms 41 and 42.

In addition, the intercepter 10 is formed mainly of a flexible material, such as synthetic resin and is deflected to be fitted into the groove 55, which material is not particularly defined.

The intercepting portions 10*a* and 10*b*, as shown in FIG. 3, are provided at both sides of support arms 41 and 42 in the rotation direction thereof and project radially outwardly beyond the inner surface of each support arm 41 or 42, thereby surely intercepting the fishing line, regardless of its thickness, and not allowing the line to enter at the gaps $S_1$ and $S_2$ inside the root of each arm 41 or 42. Incidentally, the intercepting portions 10*a* and 10*b* may alternatively be provided only at one side (the position A in FIG. 3) of one support arm 41 in the rotation direction thereof and at one side (the position B) of the other support arm 42. Also, the intercepting portions 10*a* and 10*b* may be formed in a circular arc across the support arms 41 and 42, other than the arrangement in close proximity thereto as shown, intercepting portions 10*a* and 10*b* not being particularly defined or limited as to their shape.

In the first embodiment constructed as described above, when the handle is operated to rotate the rotary frame 4 to wind the line onto the spool 5, the rotation of rotary frame 4 is transmitted from the support arms 41 and 42 to the intercepter 10 through the engaging portions 10*c* and 10*d* so that the intercepter 10 rotates together with the rotary frame 4, and also a longitudinally moving force of spool 5 is transmitted to the intercepter 10 through the cylindrical portion 54 and annular groove 55. As a result, the intercepter 10, which is in association with the spool 5, moves longitudinally relative to support arms 41 and 42.

On the other hand, when the line comes loose during casting and the loosened line is intended to enter a space at the root side of each support arm 41 or 42 through each gap $S_1$ or $S_2$ between the outer peripheral surface of cylindrical portion 54 at the inner flange 53 and the rotary frame 4, the intercepting portions 10*a* and 10*b* at the cylindrical portion 54 of flange 53 can surely prevent the line from entering through the gap $S_1$ or $S_2$ toward the root side of support arm 41 or 42.

Alternatively, the intercepter 10 may be, for example, C-like-shaped so that the intercepting portions 10*a* and 10i b and engaging portions 10*c* and 10*d* may be provided at the outer periphery, or may be divided into two in circular arc and the inner peripheries thereof may be fitted rotatably into the annular groove 55, and the outer periphery between the intercepting portions 10*a* and 10*b* may be put in proximity to the inside surfaces of support arms 41 and 42 to thereby prevent the intercepter 10 from disengaging from the annular groove 55.

Also, the intercepter 10 may alternatively be supported to the inner periphery of cylindrical portion 54 at the inner flange 53, where the cylindrical portion 54 is not indispensable.

Alternatively, the intercepter 10 may be mounted rotatably to the spool shaft 6 as shown in FIGS. 4 through 7.

In the second embodiment shown in FIGS. 4 through 7, a spool 5A is made larger in outer diameter than the first embodiment, and a trunk 51A of spool 5A is larger in axial length.

The spool 5A of such type can support an intercepter 20 rotatably to the inner flange 53A as in the first embodiment, but it is preferable to support the same to the spool shaft 6 as shown in the second embodiment.

Figure 7:
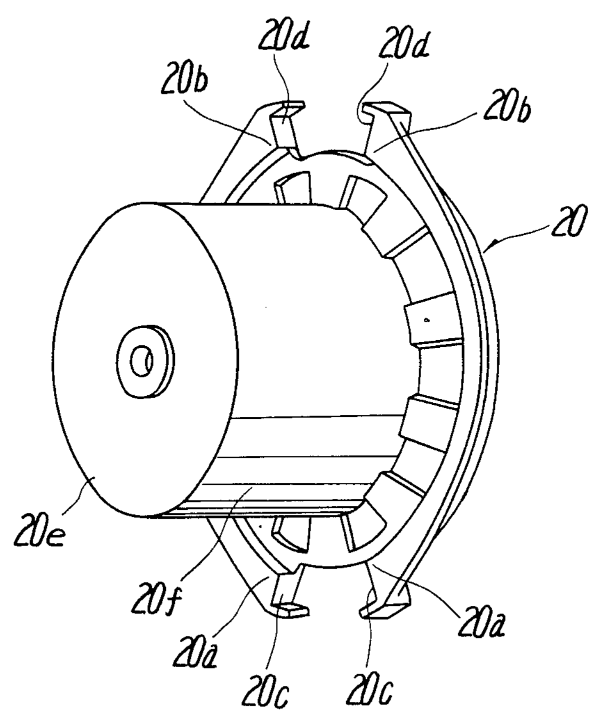
FIG. 7 is a perspective view of an intercepter only.

In this case, the intercepter 20, as shown in FIG. 7, comprises a disc-like support portion 20*e* having a central shaft bore for the spool shaft 6, a cylindrical portion 20*f* extending axially from the outer periphery of disc-like support portion 20*e*, and the intercepting portions 20*a* and 20*b* extending radially outwardly from the end portion of cylindrical portion 20*f*. The intercepting portions 20*a* and 20*b* are providing at the utmost ends thereof respectively with two engaging portions 20*c* and 20*d*, so that the engaging portions 20*c* and 20*d* engage with both side surfaces of each support arm 41 or 42 in the rotation direction thereof so as to allow the intercepter 20 to rotate together with the rotary frame 4 when rotating normally or reversely. Hence, the intercepting portions 20*a* and 20i b each are prevented from a shift in the rotation direction with respect to each support arm 41 or 42.

Also, the intercepter 20 is fitted at the shaft bore onto the spool shaft 6 in relation of being rotatable and not-axially is movable by a snap ring 12 or the like and movable along the support arms 41 and 42 in association with the axial movement of spool 5A. At the fore end portion of spool shaft 6 are provided a round shaft portion 61, a not-round shaft portion 62 and a screw thread 63 in succession. The round shaft portion 61 is fitted into the intercepter 20 rotatably relative thereto, and the not-round shaft portion 62 is fitted into the spool 5A not-rotatably relative thereto. The intercepter 20 and spool 5A are mounted to the spool shaft 6 by use of a finger nut 11 screwable with the screw thread 63. Also, the round shaft portion 61 has a groove 61*a* into which the snap ring 12 is fitted, thereby intercepting the axial movement of intercepter 20. In addition, the intercepter 20 is formed mainly of synthetic resin.

The intercepting portions 20*a* and 20*b* in FIG. 6 are constructed the same as intercepting portions 10*a* and 10*b* in the first embodiment shown in FIG. 3, thereby preventing the line from entering the gaps $S_1$ and $S_2$ between the rotary frame 4 and the support arms 41 and 42. Alternatively, the intercepting portions 20*a* and 20*b*, as in the first embodiment, may be provided at one side surface (at the positions A or B in FIG. 6) of each support arm 41 or 42 in the rotation direction thereof, or may be formed in a circular arc across the support arms 41 and 42, alternatively to the provision of intercepting portions 20*a* and 20*b* close to the arms 41 and 42. The intercepting portions are not particularly defined or limited in their formation.

In the second embodiment, the intercepter 20, as in the first embodiment, rotates together with the rotary member 4 and moves axially in association with the spool 5A longitudinally along the support arms 41 and 42.

Even when the fishing line comes loose during casting and is intended to enter the gaps $S_1$ and $S_2$ and reach the root side of each support arm 41 or 42, the intercepting portions 20*a* and 20*b* ensure the prevention of the entrance of the line into the gaps to the extent of reaching the root portions of support arms 41 or 42.

In addition, the intercepting portions 20*a* and 20*b* in the second embodiment are not particularly defined in construction.

Also, in FIGS. 4 through 6, the components identical with those in the first embodiment are designated by the same reference numerals and explanation thereof is omitted.

Alternatively, the engaging means at the intercepters 10 and 20 in the first and second embodiments may comprise grooves formed at the inner surface of each support arm 41 or 42 opposite to the spool and extending axially thereof and projections provided at the intercepters 10 and 20 and engageable with the grooves respectively.

Although several embodiments have been described, they are merely exemplary of the invention and not to be construed as limiting, the invention being defined solely by the appended claims.

What is claimed is:

1. A spinning reel, comprising a reel body, a rotary frame having a main frame and a pair of support arms connected to said main frame, said rotary frame being supported to said reel body, a spool having a trunk and an outer flange and an inner flange and supported to said reel body to be movable longitudinally thereof such that a fishing line is wound onto said spool through rotation of said rotary frame, a gap being formed between each support arm and said inner flange, and an intercepting mechanism having an intercepter for intercepting said line to prevent said line from entering through said gaps between said support arms and said inner flange at said spool to an extent to reach root sides of said support arms at which said support arms are connected to said main frame, said intercepter being supported rotatably with respect to said spool and including engaging portions engageable with at least one said support arm to allow said intercepter to rotate together with said rotary frame.

2. A spinning reel according to claim 1, wherein said intercepter has a support portion supported rotatably to the inner flange at said spool.

3. A spinning reel according to claim 2, wherein said inner flange at said spool has an annular groove for receiving therein said intercepter, said intercepter having a fitting portion fitted rotatably into said annular groove and allowing said intercepter to move longitudinally with said spool with respect to said reel body.

4. A spinning reel according to claim 2, wherein the inner flange at said spool includes a cylindrical portion extending in a same direction as said trunk, said cylindrical portion having an outer peripheral surface with an annular groove, said intercepter having a fitting portion fitted into said annular groove and formed of a ring-like plate.

5. A spinning reel according to claim 1, wherein said spool includes a spool shaft supported to said reel body, said intercepter having a support portion supported rotatably to said spool shaft.

6. A spinning reel according to claim 5, wherein said support portion includes a disc-like support portion, said intercepter further comprises a cylindrical portion extending axially from an outer periphery of said disc-like support portion, intercepting portions for intercepting said line to prevent said line from reaching said root sides of said support arms through said gaps between said inner flange and said support arms, and engaging portions engageable with said support arms.

7. A spinning reel according to claim 5, wherein said spool shaft has a means for stopping axial movement of said intercepter with respect to said spool shaft.

* * * * *